United States Patent [19]

Sueyoshi et al.

[11] 4,095,984
[45] Jun. 20, 1978

[54] DEVELOPMENT INHIBITOR RELEASING COUPLER AND PHOTOGRAPHIC ELEMENT CONTAINING SAME

[75] Inventors: Tohru Sueyoshi; Nobuo Furtachi; Akio Okumura; Tadao Shishido, all of Minami Ashigara, Japan

[73] Assignee: Fuji Photo Film Co., Ltd., Minami Ashigara, Japan

[21] Appl. No.: 755,302

[22] Filed: Dec. 29, 1976

[30] Foreign Application Priority Data

Dec. 29, 1975 Japan .................... 51-159263

[51] Int. Cl.$^2$ .................... G03C 1/40; G03C 5/30; G03C 7/00; G03C 1/34
[52] U.S. Cl. .................... 96/100 N; 96/56.5; 96/66.3; 96/109
[58] Field of Search .............. 96/66.3, 95, 109, 100, 96/100 N, 56.5

[56] References Cited

U.S. PATENT DOCUMENTS

| | | | |
|---|---|---|---|
| 2,324,123 | 7/1943 | Weissberger | 96/109 |
| 3,933,500 | 1/1976 | Shiba et al. | 96/100 |
| 3,967,965 | 7/1976 | Adachi et al. | 96/109 |

*Primary Examiner*—Dennis E. Talbert, Jr.
*Assistant Examiner*—Richard L. Schilling
*Attorney, Agent, or Firm*—Sughrue, Rothwell, Mion, Zinn and Macpeak

[57] ABSTRACT

A photographic coupler capable of releasing a development inhibitor upon reaction with an oxidation product of a color developing agent and represented by the following general formula (I) or (II)

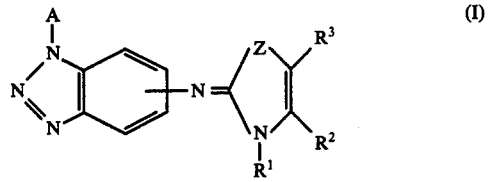

wherein A represents a coupler residue; Z represents a sulfur atom, a selenium atom or an oxygen atom; $R^1$ represents an aliphatic group; $R^2$ and $R^3$, which may be the same or different, each represents a hydrogen atom, an aliphatic group, an alkoxy group, a hydroxy group, or an aromatic group, and $R^2$ and $R^3$ can combine and represent the atoms necessary to form a benzene ring or a naphthalene ring,

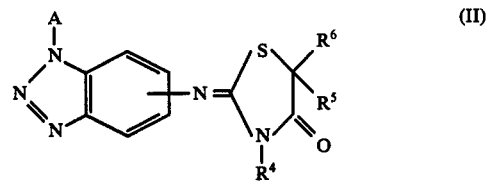

wherein A represents a coupler residue; $R^4$ represents an aliphatic group or an aromatic group; and $R^5$ and $R^6$ which may be the same or different, each represents a hydrogen atom, an aliphatic group or an aromatic group; and silver halide photographic elements containing these photographic couplers. These photographic couplers are particularly useful for controlling or modifying a number of photographic characteristics such as sharpness, graininess and color quality in a multilayer color photographic material.

15 Claims, No Drawings

DEVELOPMENT INHIBITOR RELEASING COUPLER AND PHOTOGRAPHIC ELEMENT CONTAINING SAME

BACKGROUND OF THE INVENTION

1. Field of the Invention

The present invention relates to a photographic coupler and more particularly, it relates to a novel DIR coupler (Development Inhibitor Releasing Coupler) which is capable of releasing a development inhibitor upon reaction with an oxidation product of a developing agent and a silver halide photographic element containing same.

2. Description of the Prior Art

It is conventionally known to incorporate a compound which releases a development inhibitor upon development depending on the density of an image into a photographic light-sensitive material. The compound generally reacts with an oxidation product of a color developing agent and releases a development inhibitor. As a typical example, the so-called DIR coupler in which a group capable of exhibiting development inhibiting effects upon release from the active position is introduced in the active position of the coupler is known. The DIR coupler not only forms a dye but also releases a development inhibitor upon coupling with an oxidation product of a color developing agent. The compounds described in U.S. Pat. Nos. 3,227,554; 3,701,783; 3,615,506; 3,617,291, etc. and further improved compounds thereof such as the couplers in which a triazole ring or a diazole ring is bonded to the coupling position through the nitrogen atom of the 1-position in the triazole or diazole ring as described in Japanese Patent Application (OPI) No. 122335/1974 (Corresponding to U.S. Pat. No. 3,933,500) are known as DIR couplers. Using DIR couplers many effects can be obtained such as reduced graininess of image, improved sharpness of image due to edge effects, improved color reproduction due to interimage effects, controlling image tone, and the like. However, known DIR couplers do not provide such effects, in particular, improved sharpness of the image due to edge effects, and reduced graininess of the image, sufficiently. Therefore, it is desired to provide DIR couplers which provide these effects to a sufficiently large degree.

SUMMARY OF THE INVENTION

A first object of the present invention is to provide a novel DIR coupler which can achieve a sufficiently improved sharpness of the image.

A second object of the present invention is to provide a DIR coupler which can achieve a sufficiently reduced graininess of the image.

A third object of the present invention is to provide a DIR coupler which can achieve sufficient control of the image tone and improvement of color reproduction.

A fourth object of the present invention is to provide a silver halide photographic light-sensitive material containing a novel DIR coupler and a method of forming images by conducting development processing in the presence of a novel DIR coupler.

These objects of the present invention are effectively achieved with a silver halide photographic element containing a DIR coupler capable of releasing a development inhibitor upon reaction with an oxidation product of a color developing agent and represented by the following general formula (I) or (II)

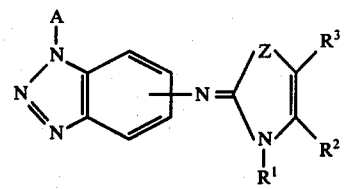

wherein A represents a coupler residue; Z represents a sulfur atom, a selenium atom or an oxygen atom; $R^1$ represents an aliphatic group; $R^2$ and $R^3$, which may be the same or different each represents a hydrogen atom, an aliphatic group, an alkoxy group, a hydroxy group, or an aromatic group or $R^2$ and $R^3$ may combine and represent the atoms necessary to form a benzene ring or a naphthalene ring;

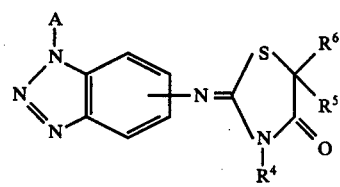

wherein A represents a coupler residue; $R^4$ represents an aliphatic group or an aromatic group; and $R^5$ and $R^6$, which may be the same or different, each represents a hydrogen atom, an aliphatic group or an aromatic group.

DETAILED DESCRIPTION OF THE INVENTION

Of the couplers represented by the general formula (I) or (II) according to the present invention, the couplers represented by the general formula (I) are preferred and those wherein Z represents a sulfur atom are particularly preferred. Further the aliphatic group for $R^1$, the aliphatic group, the alkoxy group and the aromatic group for $R^2$ and $R^3$ and the aliphatic group and the aromatic group for $R^4$, $R^5$ and $R^6$ may be substituted and when $R^2$ and $R^3$ combine, a benzene ring, which may be substituted is preferably formed.

The aliphatic group represented by $R^1$ includes an unsubstituted alkyl group having 1 to 18 carbon atoms (such as a methyl group, an ethyl group, an n-propyl group, an isopropyl group, an n-butyl group, a tert-butyl group, a heptadecyl group, etc.), a substituted alkyl group having 1 to 4 carbon atoms in the alkyl moiety, for example, a sulfoalkyl group (such as a 2-sulfoethyl group, a 3-sulfopropyl group, a 3-sulfobutyl group, a 2-hydroxy-3-sulfopropyl group, a δ-sulfobutyl group, etc.), a carboxyalkyl group (such as a 2-carboxyethyl group, a 4-carboxybutyl group, a carboxymethyl group, etc.), a hydroxyalkyl group (such as a 2-hydroxyethyl group, a 3-hydroxypropyl group, etc.), an alkoxyalkyl group including a substituted alkoxyalkyl group having 2 to 18 total carbon atoms (such as a 2-methoxyethyl group, a 3-methoxypropyl group, a 2-(2-sulfoethoxy)ethyl group, a 2-[2-(3-sulfopropoxy)ethoxy]ethyl group, a hydroxymethoxymethyl group, a 2-hydroxyethoxymethyl group, a 2-(2-hydroxydiethoxy)-ethyl group, a 2-(2-acetoxyethoxy)ethyl group, an acetoxymethoxymethyl group, etc.), an acyloxyalkyl group having 2 to 18 total carbon atoms (such as a 2-acetoxyethyl group, a 4-propionyloxybutyl group, etc.), a dialkylaminoalkyl group having a total of 3 to 18 carbon atoms (such as a dimethylaminoethyl group, a diethylaminopropyl group, etc.), a halo-substituted alkyl group (such as a trifluoromethyl group, etc.), a sulfatoalkyl group (such as a β-sulfatoethyl group, a 4-sulfatobutyl group, etc.), an aralkyl group having a total of 7 to 16 carbon atoms (such as a benzyl group, a phenethyl group, a p-sulfobenzyl group, etc.), an alkenyl group having 1 to 18 carbon atoms (such as a vinylmethyl group, etc.), and the like.

Preferred examples of the aliphatic group represented by $R^1$ include an aralkyl group having 7 to 16 total carbon atoms and an alkyl group having 1 to 18 carbon atoms.

The aliphatic group each represented by $R^2$ and $R^3$ includes an unsubstituted alkyl group having 1 to 18 carbon atoms (such as a methyl group, an ethyl group, an isopropyl group, an n-butyl group, a tert-butyl group, a heptadecyl group, etc.), a substituted alkyl group having 1 to 12 carbon atoms in the alkyl moiety, for example, a sulfoalkyl group (such as a 2-sulfoethyl group, a 3-sulfopropyl group, a 3-sulfobutyl group, a 4-sulfobutyl group, a 2-hydroxy-3-sulfopropyl group, etc.), a carboxyalkyl group (such as a 2-carboxyethyl group, a 4-carboxybutyl group, a carboxymethyl group, etc.), a hydroxyalkyl group (such as a β-hydroxyethyl group, a γ-hydroxypropyl group, etc.), an alkoxyalkyl group including a substituted alkoxyalkyl group having 2 to 18 total carbon atoms (such as a β-methoxyethyl group, a γ-methoxypropyl group, a 2-(2-sulfoethoxy)ethyl group, a 2-[2-(3-sulfopropoxy)ethoxy]ethyl group, a hydroxymethoxymethyl group, a 2-hydroxyethoxymethyl group, a 2-(2-hydroxyethoxy)ethyl group, a 2-(2-acetoxyethoxy)ethyl group, an acetoxymethoxymethyl group, etc.), an acyloxyalkyl group (having 2 to 18 total carbon atoms (such as a 2-acetoxyethyl group, a 4-propionyloxybutyl group, etc.), a dialkylaminoalkyl group having 3 to 18 total carbon atoms (such as a dimethylaminoethyl group, a diethylaminopropyl group, etc.), a halo-substituted alkyl group (such as a trifluoromethyl group, etc.), a sulfatoalkyl group (such as a β-sulfatoethyl group, an ω-sulfatobutyl group, etc.), an aralkyl group (having 7 to 16 total carbon atoms (such as a benzyl group, a phenethyl group, a p-sulfobenzyl group, etc.), an alkenyl group having 1 to 18 carbon atoms (such as a vinylmethyl group, etc.), and the like.

The aromatic group each represented by $R^2$ and $R^3$ includes a monocyclic or bicyclic aryl group having 6 to 10 carbon atoms, preferably a monocyclic group, and can be an unsubstituted aryl group (such as a phenyl group, a naphthyl group, etc.), and a substituted aryl group, for example, a phenyl group having, as a substituent, an alkyl group having 1 to 4 carbon atoms (such as a methyl group, etc.), an alkoxy group having 1 to 4 carbon atoms (such as a methoxy group, an ethoxy group, etc.), a hydroxy group, a halogen atom (such as a chlorine atom, etc.), a sulfo group, and the like. Specific examples of substituted phenyl groups are a p-tolyl group, a p-methoxyphenyl group, a p-hydroxyphenyl group, a 2,4-dimethoxyphenyl group, a p-chlorophenyl group, a p-sulfophenyl group, etc.

$R^2$ and $R^3$ each represents an alkoxy group having 1 to 18 carbon atoms, for example, an unsubstituted alkoxy group (such as a methoxy group, a ethoxy group, a propargyloxy group, etc.), or a substituted alkoxy group (such as a benzyloxy group, an α-naphthylmethyloxy group, etc.).

Of the couplers represented by the general formula (I) of the present invention, preferred couplers can be represented by the following general formula (Ia):

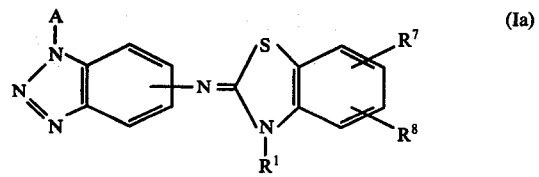

wherein A and $R^1$ each has the same meaning as defined in general formula (I); $R^7$ and $R^8$, which may be the same or different, each represents a hydrogen atom, a halogen atom, an aliphatic group, an alkoxy group, a hydroxy group, a nitro group, a carboxyl group, an alkoxycarbonyl group, an acylamino group, a sulfonamido group or an aryl group.

The halogen atom each represented by $R^7$ and $R^8$ can be, for example, a chlorine atom, a bromine atom, an iodine atom, et. The aliphatic group, the alkoxy group and the aryl group each represented by $R^7$ and $R^8$ are the same as defined for $R^2$ and $R^3$. Preferred groups for $R^7$ and $R^8$ are a hydrogen atom, a methyl group, an ethyl group, a chlorine atom, a methoxy group, an ethoxy group, a hydroxy group, an ethoxycarbonyl group, an acetamido group and an ethylsulfonamido group.

The aliphatic hydrocarbon group and the aromatic hydrocarbon group represented by $R^4$, $R^5$ and $R^6$ in general formula (II) are the same as defined for $R^2$ and $R^3$.

The residue represented by A in general formula (I) and (II) is connected to the nitrogen atom of the 1-position of the benzotriazole nucleus in general formula (I) or (II) at its coupling-active position. For example, a residue of a 5-pyrazolone coupler, a cyanoacetylcoumarone coupler, an indazolone coupler, a benzimidazolopyrazolone coupler, an open-chain acylacetonitrile coupler, an open-chain acylacetamide coupler (particularly, a benzoylacetanilide coupler or a pivaloylacetanilide coupler), a naphthol coupler, a phenol coupler, and the like can be used.

A residue represented by the following general formula (III) is particularly useful for a magenta coupler residue:

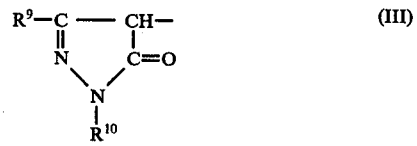

wherein $R^9$ represents a hydroxy group, a primary, secondary or tertiary alkyl group having 1 to 32 carbon atoms (such as methyl, propyl, n-butyl, tert-butyl, hexyl, 2-hydroxyethyl, 2-phenylethyl, etc.), an aryl group having 6 to 32 carbon atoms (such as phenyl, methoxyphenyl, etc.), a heterocyclic group, for example, a 5- or 6-membered ring containing a nitrogen atom, an oxygen atom, etc. as a hetero atom (such as quinolyl, pyridyl, benzofuranyl, oxazolyl, etc.), an amino group (such as alkylamino having 1 to 22 carbon atoms, e.g., methylamino, diethylamino, dibutylamino, etc., and arylamino having 6 to 22 carbon atoms, e.g., phenylamino, tolylamino, 4-(3-sulfobenzamino)anilino, 2-chloro-5-acylaminoanilino, 2-chloro-5-alkoxycarbonylanilino, 2-trifluoromethylphenylamino, a heterocyclic amino, e.g., 1-pyrrolidinyl, 4-morpholinyl, 1-piperidinyl, etc.), a carbonamido group (such as alkylcarbonamido, e.g., ethylcarbonamido, aryl carbonamido such as phenylcarbonamido, heterocyclic carbonamido, e.g., benzothiazolylcarbonamido, etc.), a sulfonamido group (such as alkylsulfonamido, e.g., ethylsulfonamido, hexamethylsulfonamido, arylsulfonamido, e.g., phenylsulfonamido, heterocyclic sulfonamido, etc.), a ureido group (such as alkylureido, e.g., ethylureido, arylureido, e.g., phenylureido, heterocyclic ureido, etc.), or an alkoxy group having 1 to 22 carbon atoms (such as methoxy, ethoxy, etc.); $R^{10}$ represents a hydrogen atom, an aryl group (such as naphthyl, phenyl, 2,4,6-trichlorophenyl, 2-chloro-4,6-dimethylphenyl, 2,6-dichloro-4-methoxyphenyl, 4-methylphenyl, 4-acylaminophenyl, 4-alkylaminophenyl, 4-trichloromethylphenyl, 3,5-dibromophenyl, etc.), a heterocyclic group, for example, a 5- or 6-membered ring containing a nitrogen atom, an oxygen atom, a sulfur atom, etc. as a hetero atom (such as benzofuranyl, naphthoxazolyl, quinolyl, thiazolyl, etc.), an alkyl group (such as ethyl, benzyl, etc.).

A residue represented by the following general formula (IV) is useful for a yellow coupler residue:

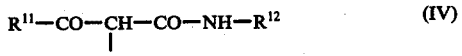

wherein $R^{11}$ represents a primary, secondary or tertiary alkyl group having 1 to 18 carbon atoms (such as tert-butyl, 1,1-dimethylpropyl, 1,1-dimethyl-1-methoxyphenoxymethyl, 1,1-dimethyl-1-ethylthiomethyl, etc.), an aryl group having 6 to 40 carbon atoms (such as phenyl, alkylphenyl, e.g., 3-methylphenyl, 3-octadecylphenyl, etc., alkoxyphenyl, e.g., 2-methoxyphenyl, 4-methoxyphenyl, etc., halophenyl, 2-halo-5-alkamidophenyl, 2-chloro-5-(α-(2,4-di-tert-amylphenoxy)butyramido]phenyl, 2-methoxy-5-alkamidophenyl, 2-chloro-5-sulfonamidophenyl, naphthyl, etc.), an amino group (such as arylamino having 6 to 40 carbon atoms, e.g., anilino p-methoxyanilino, alkylamino having 1 to 18 carbon atoms, e.g., butylamino, etc.); $R^{12}$ represents an aryl group having 6 to 40 carbon atoms (such as mononuclear aryl, e.g., 2-chlorophenyl, 2-halo-5-alkylamidophenyl, e.g., 2-chloro-5-[α-(2,4-di-tert-amylphenoxy)acetamido]phenyl, 2-chloro-5-(4-methylphenylsulfonamido)phenyl, 2-methoxy-5-(2,4-di-tert-amylphenoxy)acetamidophenyl, 2-methoxyphenyl, 2-ethoxyphenyl, etc.). The above described halo-substitution includes substitution with chlorine, bromine, fluorine, etc.

When A is a residue represented by general formula (IV) of the DIR coupler of the present invention, it is preferred that $R^{11}$ be a tertiary alkyl group (including a substituted tertiary alkyl group such as pivaloyl) or an aryl group (such as phenyl, naphthyl, etc., which can be substituted and preferably is a phenyl group substituted with an alkyl group having up to 40 carbon atoms, e.g., ethyl, octyl, etc.).

A residue represented by the following general formula (V) or (VI) is useful for a cyan coupler residue:

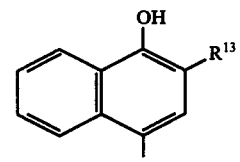

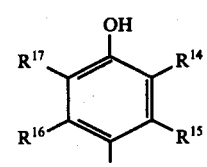

wherein $R^{13}$ represents a substituent used for a cyan coupler, for example, a carbamyl group (such as alkylcarbamyl, arylcarbamyl, e.g., phenylcarbamyl, heterocyclic carbamyl, e.g., benzothiazolylcarbamyl, etc.), a sulfamyl group (such as alkylsulfamyl, arylsulfamyl, e.g., phenylsulfamyl, heterocyclic sulfamyl, etc.), an alkoxycarbonyl group, an aryloxycarbonyl group and the like; $R^{14}$ represents an alkyl group, an aryl group, a heterocyclic group, an amino group (such as amino, alkylamino, arylamino, etc.), a carbonamido group (such as alkylcarbonamido, arylcarbonamido, etc.), a sulfonamido group, a sulfamyl group (such as alkylsulfamyl, arylsulfamyl, etc.), a carbamyl group, and the like. $R^{15}$, $R^{16}$ and $R^{17}$ each represents the groups defined for $R^{14}$, a halogen atom, an alkoxy group, and the like.

It is advantageous that the coupler used in the present invention be diffusion resistant. In order to render the coupler diffusion resistant, a group containing a hydrophobic residue having 8 to 32 carbon atoms is introduced into the coupler molecule. Such a residue is usually designated a ballast group. The ballast group can be combined with the coupler skeleton directly or through an imino bond, an ether bond, a carbonamido bond, a sulfonamido bond, a ureido bond, an ester bond, an imido bond, a carbamoyl bond, a sulfamoyl bond, etc. The ballast group can be connected to a group capable of being released upon development. Examples of ballast groups are described in many patent specifications such as U.S. Pat. No. 2,920,961, Japanese Patent Application (OPI) Nos. 123034/1974 and 69383/1973, etc.

Some examples of ballast groups are shown in specific examples of the coupler of the present invention.

The coupler of the present invention can be a noncolor-forming coupler.

Specific examples of the couplers according to the present invention are illustrated in the following. However, the present invention is not to be construed to be limited to these specific examples only.

1 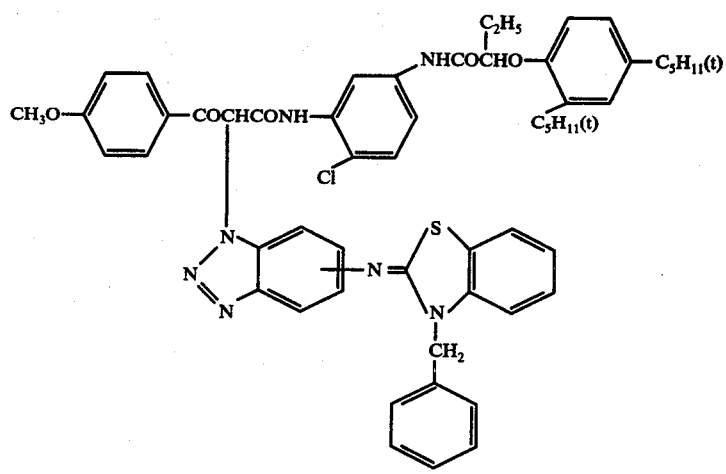
2 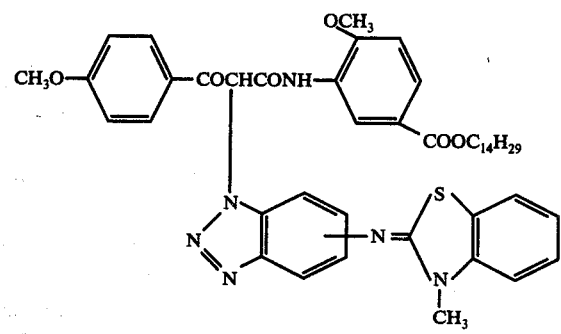
3 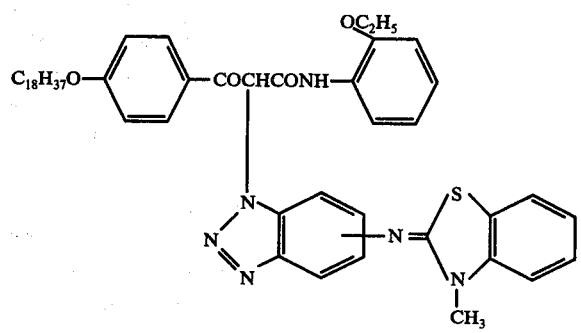
4 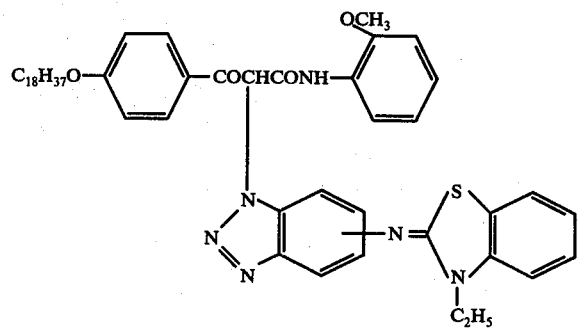

5 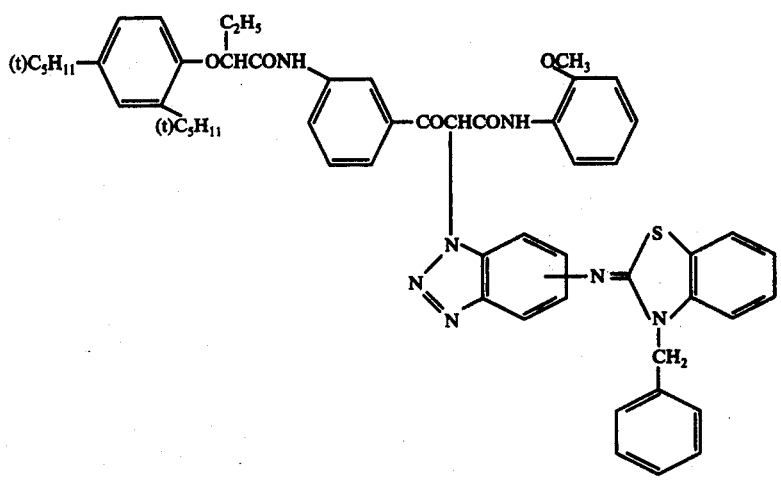
6 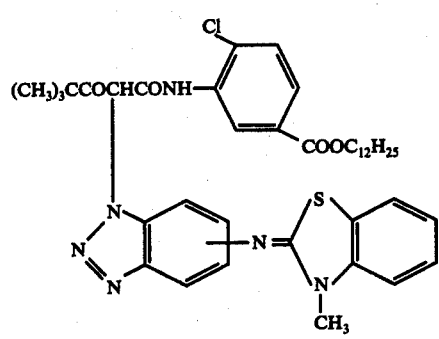
7 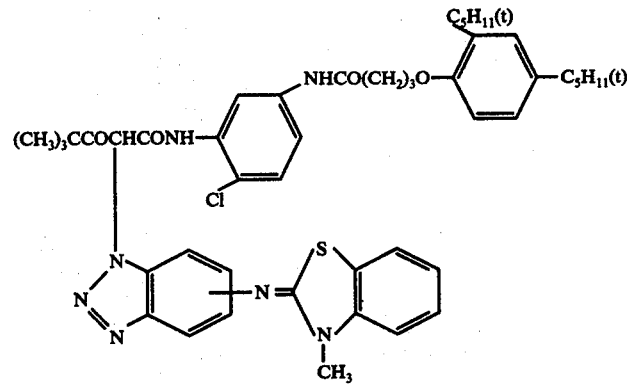
8 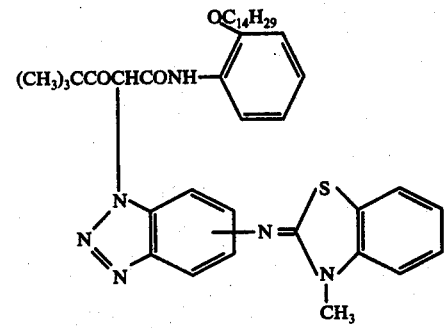

9 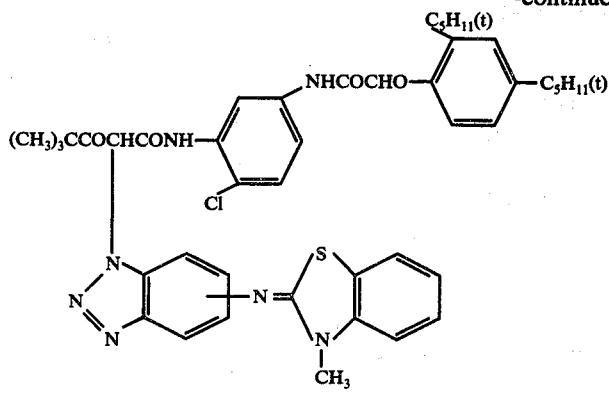
10 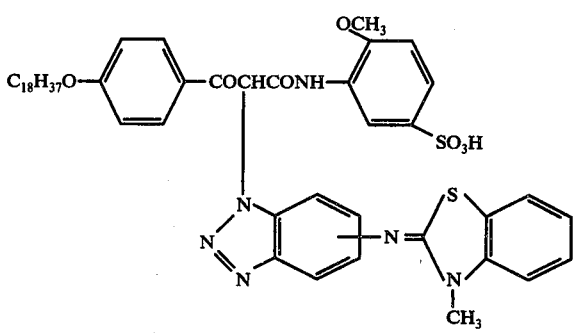
11 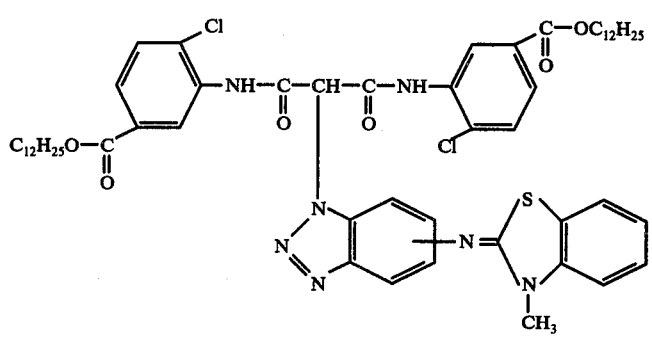
12 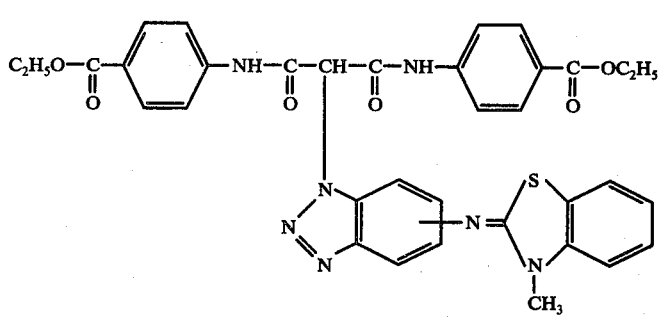
13 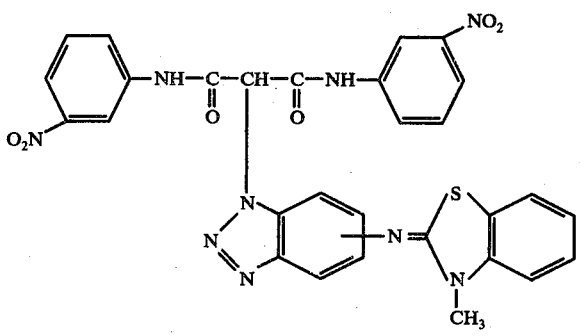

-continued
14 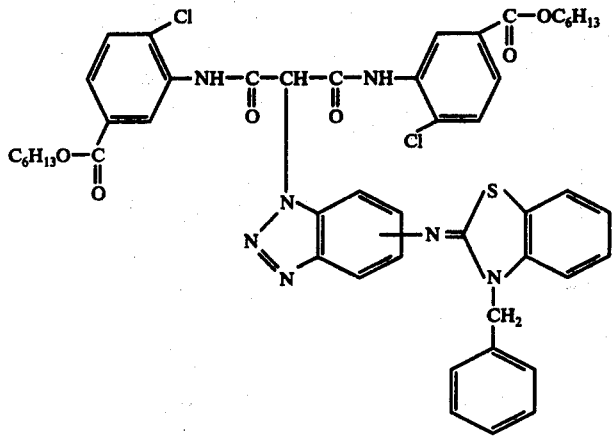
15 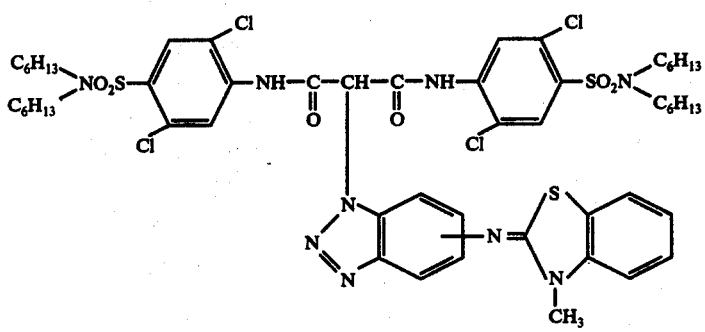
16 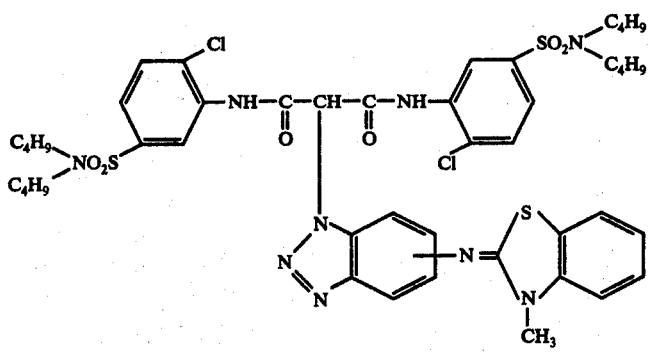
17 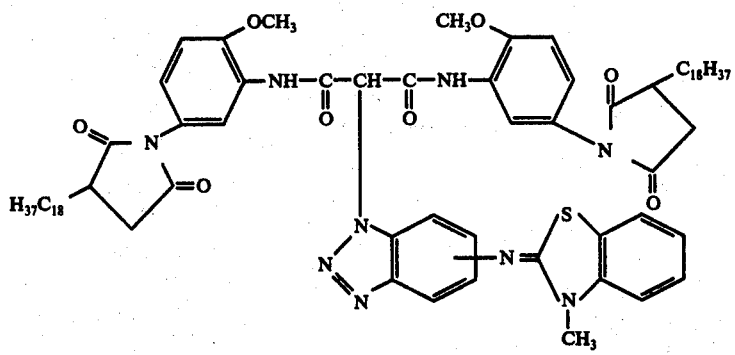

-continued
18
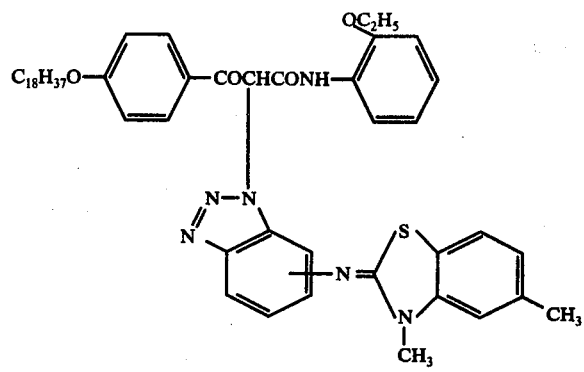
19
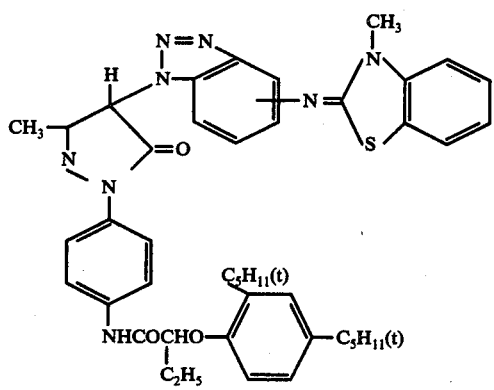
20
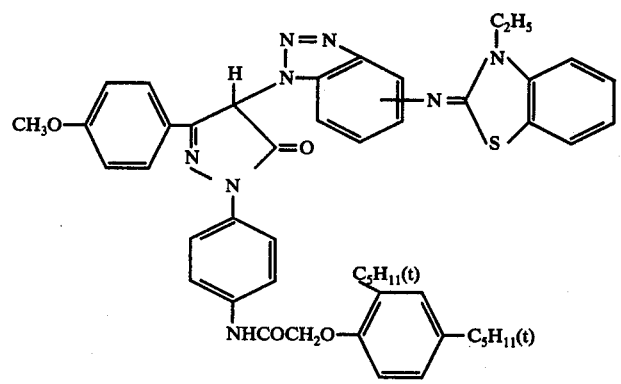
21
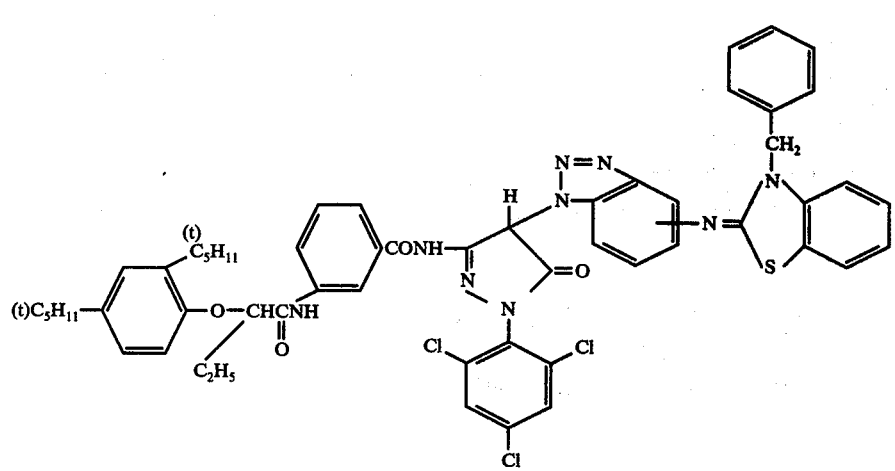

-continued
22
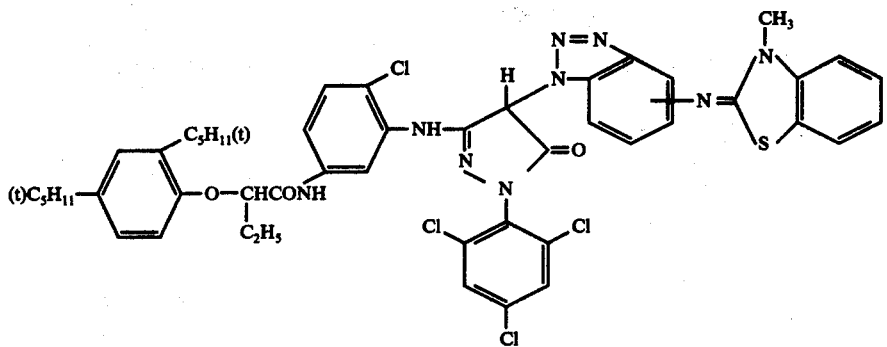
23
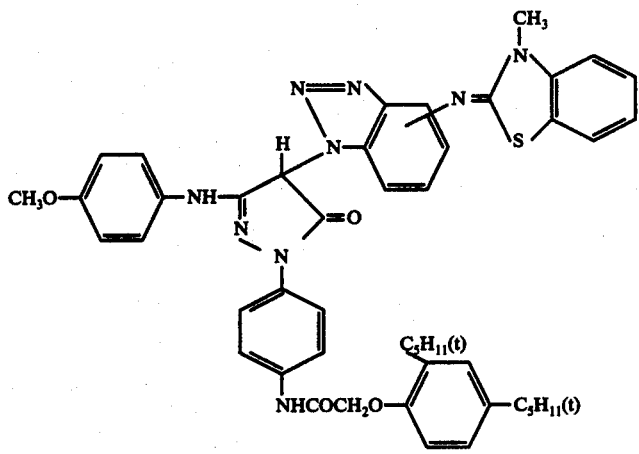
24
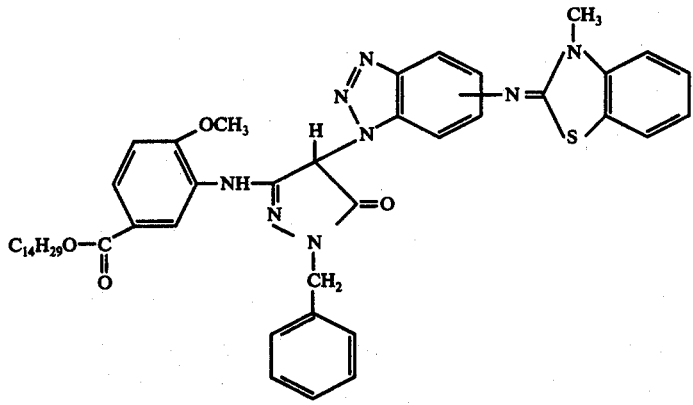
25
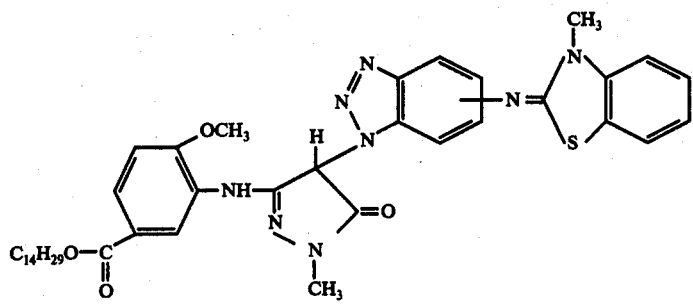

26 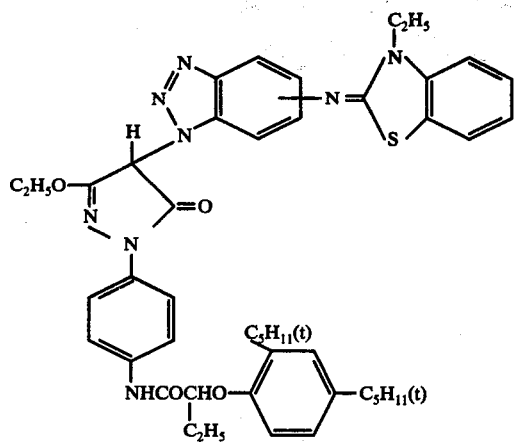
27 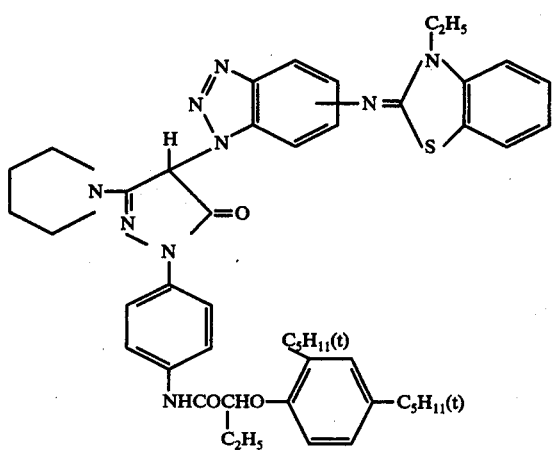
28 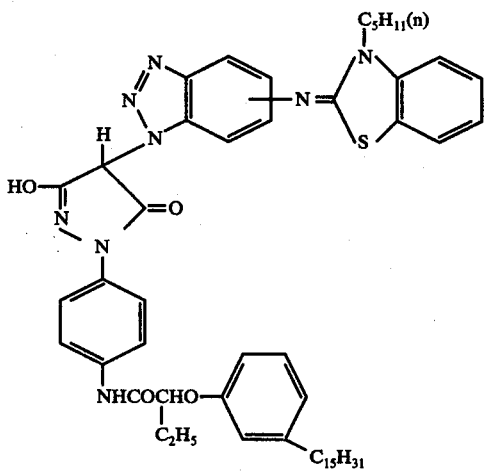

29 -continued

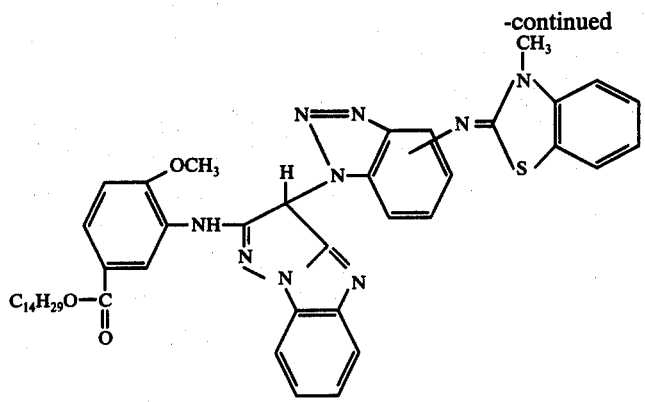

When the DIR coupler of the present invention is a yellow color forming coupler, it is particularly preferred that the coupler residue represented by A in general formulae (I) and (II) is a residue represented by the following general formula (IVa)

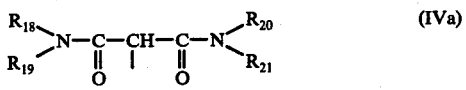

wherein $R_{18}$, $R_{19}$, $R_{20}$ and $R_{21}$ each represents a hydrogen atom, an aliphatic residue, an aromatic residue or a heterocyclic residue. $R_{18}$, $R_{19}$, $R_{20}$ and $R_{21}$ can be the same or different from each other.

In more detail, the aliphatic residue represented by $R_{18}$, $R_{19}$, $R_{20}$ and $R_{21}$ in the above-described general formula (IVa) preferably contains 1 to 25 carbon atoms and can be unsaturated, branched or cyclic. The aliphatic residue can be substituted with one or more substituents, for example, an alkoxy group (such as methoxy, isopropoxy, etc.), a halogen atom (such as chlorine, bromine, etc.), a hydroxy group, a carboxy group, a sulfo group, a heterocyclic group containing one or more of an oxygen atom, a nitrogen atom, etc., as a heteroatom (such as tetrahydrofuryl, pyridyl, etc.), an aryl group (such as phenyl, tolyl, etc.), and the like. Preferred examples of aliphatic residues are, for example, methyl, ethyl, isopropyl, tetradecyl, octadecyl, etc.

The coupler of the present invention can be prepared by reacting the corresponding mother coupler, in which the coupling position is unsubstituted, with a halogen atom in a solvent such as chloroform, carbon tetrachloride, etc. to halogenate (preferably, brominate) the coupling position and then reacting the halogenated compound with the corresponding benzotriazole compound (i.e., the compound represented by general formula (I) or (II) wherein A is a hydrogen atom) in the presence of a base such as triethylamine, sodium hydroxide, potassium hydroxide, etc. In the reaction with the benzotriazole compound, preferred solvents are dimethylformamide, acetonitrile, tetrahydrofuran, etc. and a preferred temperature is in the range from about 20° to about 150° C.

Synthesis examples of the couplers according to the present invention are illustrated in the following. Unless otherwise indicated herein, all parts, percents, ratios and the like are by weight.

SYNTHESIS EXAMPLE 1

(Preparation of Coupler 6)

(I) Preparation of 5-(3-Methylbenzothiazolinylidene)aminobenzotriazole 175 g of anhydrous 3-methyl-2-(3-sulfopropylthio) benzothiazolium hydroxide was added to a mixture of 100 g of 5-aminobenzotriazole di-hydrochloride, 120 g of sodium acetate and 1000 ml of water under heating at 50° C with stirring in a 2000 ml flask. After stirring for 1 hour at 85° C the mixture was cooled (15° C) with water. The precipitate formed was collected by filtration, washed with water and then with acetonitrile to yield 135 g of crystals. These crystals were dissolved by heating (90° C) in 350 ml of dimethylformamide and the solution was treated with active carbon and filtered. By addition of 1400 ml of acetonitrile to the filtrate, crystals were formed. The crystals were collected to yield 121 g of the desired compound. The melting point was 240.5° C.

(2) Preparation of Coupler 6

18.6 g of α-pivaloyl-2-chloro-5-dodecyloxycarbonylacetanilide was dissolved in 50 ml of chloroform. To the solution was added dropwise 6.4 g of bromine at 5° C with stirring. After the completion of the addition of bromine, the solution was washed three times with 300 ml of water. The solution was added dropwise to a solution containing 19.1 g of 5-(3-methylbenzothiazolinylidene)aminobenzotriazole and 6.9 g of triethylamine dissolved in 50 ml of dimethylformamide at 20° to 25° C with stirring. After the completion of the addition, the reaction mixture was stirred for 30 min. and washed with a 3% aqueous sodium hydroxide solution, then with a 5% aqueous hydrochloric acid solution and with water. The solution was concentrated under reduced pressure and the residue was recrystallized from a solvent mixture of acetonitrile and ethyl acetate to yield 15.6 g of the desired compound. The melting point was 111° to 116° C.

SYNTHESIS EXAMPLE 2

Preparation of Coupler 3

55.1 g of α-(4-octadecyloxybenzoyl)-2-ethoxyacetanilide was dissolved in 200 ml of chloroform. To the solution was added dropwise 16.5 g of bromine at 5° C with stirring. After the completion of the addition of bromine, the solution was washed with 500 ml of water. The solution was added dropwise to a solution containing 56.2 g of 5-(3-methylbenzothiazolinylidene)aminobenzotriazole and 20.2 g of triethylamine dissolved in 200 ml of dimethylformamide at 20° to 23° C. After the completion of the addition, the reaction mixture was stirred for 1 hour and washed with a 3% aqueous sodium hydroxide solution, with a 5% aqueous hydrochloric acid solution and with water. The solution was concentrated under reduced pressure and the residue was recrystallized from a solvent mixture of isopropanol and ethyl acetate (1 : 2 by volume) to yield 36.3 g of the desired compound. The melting point was 99° to 103° C.

SYNTHESIS EXAMPLE 3

Preparation of Coupler 19

(I) Preparation of Ethyl-α-[5- or 6-(3-methylbenzothiazolinylidene)amino-1-benzotriazolyl]acetacetate (Intermediate (1))

28.1 g of 5-(3-methylbenzothiazolinylidene)aminobenzotriazole and 15.2 g of triethylamine were added to 100 ml of ethylene chloride. The solution was heated at 65° to 70° C and 16.5 g of ethyl α-chloracetacetate was added dropwise thereto.

After being heated at the above-described temperature for 3 hours with stirring, the solution was cooled. The triethylamine hydrochloride deposited was removed by filtration and the filtrate was sufficiently washed with water and concentrated. Without any further purification the compound was used in the next step.

(2) Preparation of 1-(4-Nitrophenyl)-3-methyl-4-[5-or 6-(3-methylbenzothiazolinylidene)amino-1-benzotriazolyl]-5-oxo-2-pyrazoline (Intermediate (2))

40 g of the above-described Intermediate (1) and 15.3 g of 4-nitrophenyl hydrazine were added to 200 ml of ethylene chloride and 7.5 g of acetic acid was added thereto. After being refluxed by heating for 1 hour, the reaction solution was cooled and the crystals depsited were collected by filtration (21 g). The filtrate was concentrated and crystallized with acetonitrile to yield 14 g of the desired compound, additionally. The melting point was 225° to 227° C.

(3) Preparation of Coupler 19

50 g of the above-described Intermediate (2) was added to 300 ml of acetic acid and 1.5 g of ammonium chloride and 15 ml of water were added thereto. The mixture was heated at 60 to 80° C with stirring under a nitrogen atmosphere. 47 g of granulated iron was gradually added to the mixture and further heated for 20 min. The reaction solution was cooled to 25 to 30° C and 9.8 g of sodium acetate was added thereto followed by stirring for 30 min. To the mixture was added 40.6 g of α-(2,4-di-tert-amylphenoxy)butyryl chloride and stirred for 1 hour at 25° to 30° C. After the completion of the reaction, the reaction mixture was added to 700 ml of ethyl acetate and washed sufficiently with water. The ethyl acetate layer was dried with anhydrous sodium sulfate and concentrated to a solid, which was recrystallized from a solvent mixture of benzene and acetonitrile (1:1 by volume) to yield 64 g of white crystals. The melting point was 194° to 196° C.

SYNTHESIS EXAMPLE 4

Preparation of Coupler 23

(I) Preparation of 1-(4-Nitrophenyl)-3-(N-acetyl-4-methoxyanilino)5-oxo-2-pyrazoline (Intermediate (1))

32.6 g of 1-(4-nitrophenyl)-3-(4-methoxyanilino)-5-oxo-2-pyrazoline was dispersed in 110 g of acetic anhydride and 2.7 g of zinc chloride was added thereto and heated (70° to 80° C) on a steam bath with stirring. The mixture became a uniform solution as the reaction proceeded. After the completion of the reaction, 500 ml of ethyl acetate and 500 ml of water were added the reaction mixture and concentrated aqueous ammonia (28%) was added dropwise thereto under cooling to completely decompose the excess acetic anhydride. The crystals deposited in the ethyl acetate were collected by filtration. The filtrate was sufficiently washed with water and the ethyl acetate solution was concentrated to one-third of its original volume and cooled (5° C) to yield a second amount of crystals which was added to the first crystals obtained. Total yield of the product was 31 g. The melting point was 165° to 167° C.

(2) Preparation of 1-(4-Nitrophenyl)-3-(N-acetyl-4-methoxyanilino)-4-bromo-5-oxo-2-pyrazoline (Intermediate (2))

18.5 g of the above-described Intermediate (1) was dissolved in 100 ml of acetic acid and 8 g of bromine was added dropwise thereto at 15° to 20° C. After being stirred for 1 hour at the above-described temperature, the reaction solution was poured into a large amount of ice water and stirred vigorously. The crystals deposited were collected by filtration, sufficiently washed with water, dried and recrystallized from acetonitrile to yield 19.5 g of yellow crystals. The melting point was 163° to 164° C.

(3) Preparation of 1-(4-Nitrophenyl)-3-(4-methoxyanilino)-4-[5-or 6-(3-methylbenzothiazolinylidene)amino-1-benzotriazolyl]5-oxo-2-pyrazoline (Intermediate (3))

44.8 g of Intermediate (2) obtained in the above-described step and 58 g of 5-(3-methylbenzothiazolinylidene)aminobenzotriazole were mixed with 60 g of hexamethylphosphotriamide and the mixture was heated at 110° C in an oil bath for 4 hours with stirring. 200 ml of ethyl acetate was added to the reaction mixture and upon cooling (10° C) white crystals were deposited. The crystals were removed by filtration and to the filtrate of the ethyl acetate solution was added 40 ml of concentrated hydrochloric acid (36%) and stirred at 20° to 30° C for 3 hours to deposit yellow crystals. Almost all of these crystals were the hydrochloride of the desired compound. The crystals were collected by filtration and 300 ml of a 10% methanol solution of potassium hydroxide was added to the crystals and the mixture was stirred at 30° to 50° C. After stirring for 5 hours, the acetyl group was completely hydrolyzed. The reaction solution was neutralized with acetic acid and added to an excess amount of ice water. The solid deposited was collected by filtration and washed sufficiently with water. After drying the solid was recrystallized from acetonitrile to yield 32 g of yellow crystals. The melting point was 210° to 215° C.

(4) Preparation of Coupler 23

12.1 g of Intermediate (3) obtained in the above-described Step 3 was reduced by the method described in Step 3 of Synthesis Example 3 using 12 g of granulated iron and acetic acid. The product was reacted with 6.2 g of (2,4-di-tert-amylphenoxy)acetyl chloride and treated in the same manner as described in Step 3 of Synthesis Example 3. By recrystallization from acetonitrile-ethyl acetate (10:1 by volume) 7.5 g of crystals were obtained. The melting point was 170° to 175° C.

SYNTHESIS EXAMPLE 5

Preparation of Coupler 11

(1) Preparation of 2',2"-Dichloro-5',5"-didodecyloxycarbonylmalonanilide 170 g of (0.5 mol) of 2-chloro-5-dodecyloxycarbonylaniline and 40 g (0.25 mol) of diethyl malonate were stirred in a 1 liter, three-necked flask with heating at 220° C for about two hours and the ethanol formed was distilled off. After completely removing the ethanol by stirring under reduced pressure (about 50 mm Hg) with heating (170° C) for about 10 hours, the residue was cooled to room temperature (about 20° to 30° C). The solid deposited was recrystallized from ethanol to yield 151.6 g (81%) of the desired compound having a melting point of 94° to 95° C.

(2) Preparation of 2-Bromo-2',2''-dichloro-5',5''-didodecyloxycarbonylmalonanilide 6.7 g (0.009 mol) of malonic acid di-2-chloro-5-dodecyloxycarbonylanilide was dissolved in 170 cc of acetic acid and to the solution under heating at 45° C with stirring, a solution containing 1.6 g (0.01 mol) of bromine dissolved in 30 ml of acetic acid was added dropwise thereto over a period of about 30 min. The reaction solution was poured into 200 cc of ice water and the solid deposited was collected with filtration. The solid was recrystallized from acetonitrile to yield 6.8 g (92%) of the desired compound.

(3) Preparation of Coupler 11

30 g (0.036 mol) of 2-bromo-2',2''-dichloro-5',5''-didodecyloxycarbonyl-malonanilide and 15.3 g (0.054 mol) of 5-(3-methyl-2-benzothiazolinylidene)aminobenzotriazole (prepared in the same manner as in Synthesis Example 1) were suspended in 300 ml of tetrahydrofuran (THF) and, with stirring at room temperature, 7.3 g (0.092 mol) of triethylamine was added dropwise thereto. After stirring about 5 hours, 500 ml of water and 200 ml of chloroform were added and 20 ml of concentrated hydrochloric acid was added with stirring. The solid deposited was collected with filtration and the filtrate was washed with 2N hydrochloric acid and then twice with water and dried. The solvent was removed under reduced pressure and the residue was recrystallized from ethanol to yield 30.3 g (82%) of the desired compound having a melting point of 118° to 123° C.

The DIR coupler of the present invention can be incorporated either into a photographic emulsion layer or into a developer solution. In order to render the DIR coupler of the present invention diffusion resistant in a photographic emulsion layer, any known ballast group can be introduced into the molecule.

The DIR coupler of the present invention can be introduced into a photographic layer using any known dispersing method. The DIR coupler of the present invention can be used individually or as a combination two or more thereof. Further, the DIR coupler of the present invention can be incorporated either into a photographic emulsion layer as a dispersion containing another coupler together therewith or into a photographic subsidiary layer such as an intermediate layer as a dispersion thereof.

The DIR coupler of the present invention is used in a ratio of 0.01 to 100 mol%, preferably 0.1 to 30 mol% to the coupler in each light-sensitive layer such as a yellow coupler in a blue-sensitive layer, a magenta coupler in a green sensitive layer or a cyan coupler in a red-sensitive layer of a color light-sensitive material.

Dye forming couplers which can be used together with the photographic coupler of the present invention are described in the following. The coupler can be either a four-equivalent coupler or a two-equivalent coupler. Also the coupler can be a colored coupler for color correction or a DIR coupler other than that of the present invention.

A known open-chain ketomethylene type coupler can be used as a yellow chain coupler. Of these couplers, a benzoylacetanilide type compound and a pivaloylacetanilide type compound are advantageous. Specific examples of yellow color couplers which can be used are described in U.S. Pat. Nos. 2,875,057; 3,265,506; 3,341,331; 3,369,895; 3,408,194; 3,551,155; 3,582,322 and 3,725,072, German Patent Publication No. 1,547,868, German Patent Application (OLS) No. 2,057,941; 2,162,899; 2,213,461; 2,219,917; 2,261,361 and 2,263,875, etc.

A pyrazolone type compound, an indazolone type compound, a cyanoacetyl type compound, and the like can be used as a magenta color coupler. Of these couplers a pyrazolone type compound is particularly advantageous. Specific examples of magenta color couplers which can be used are described in U.S. Pat. Nos. 2,439,098; 2,600,788; 2,983,608; 3,311,476; 3,419,391; 3,519,429; 3,558,319; 3,582,322 and 3,615,506, British Pat. No. 956,261, German Pat. No. 1,810,464, German patent application (OLS) Nos. 2,408,665; 2,418,959 and 2,424,467, Japanese Patent Publication No. 2016/1969, etc.

A phenol derivative, a naphthol derivative, and the like can be used as a cyan color coupler. Specific examples of cyan color couplers are described in U.S. Pat. Nos. 2,369,924; 2,434,272; 2,474,293; 2,600,788; 2,698,794; 2,706,684; 2,895,826; 3,034,892; 3,214,437; 3,253,924; 3,311,476; 3,386,830; 3,458,315; 3,560,212; 3,582,322; 3,583,971 and 3,591,383, German Patent Application (OLS) Nos. 2,163,811 and 2,414,006; Japanese Patent Publication Nos. 6031/1965 and 28836/1970, etc.

As a colored coupler, the compounds described, for example, in Japanese Patent Publication No. 2016/1969, U.S. Pat. Nos. 2,434,272; 3,476,560 and 3,476,564, German Patent Application (OLS) No. 2,418,959 (the above described are magenta color forming colored couplers), Japanese Patent Publication Nos. 22335/1963; 20591/1966; 11304/1967 and 32461/1969, U.S. Pat. Nos. 3,034,892; and 3,386,830 (the above described are cyan color forming colored coupler) can be used.

As a DIR coupler other than that of the present invention, the compounds described, for example, in U.S. Pat. Nos. 3,148,062; 3,214,437; 3,227,554; 3,253,924; 3,617,291; 3,622,328; 3,639,417; 3,701,783; 3,705,201; 3,770,436 and 3,790,384, Japanese Patent Publication No. 28836/1970, German Patent Application (OLS) Nos. 2,414,006 and 2,417,914, etc. can be used.

Two or more of the above-described couplers and the like can be incorporated in the same layer or the same compound can be incorporated in two or more layers in order to fulfill the characteristics required in a light-sensitive material.

In order to incorporate the coupler into an emulsion layer, known methods, for example, the method described in U.S. Pat. No. 2,322,027 can be used. That is, the coupler is dissolved in an organic solvent having a boiling point higher than about 180° C for example, an alkyl ester of phthalic acid (such as dibutyl phthalate, dioctyl phthalate, etc.), an ester of trimellitic acid (such as tri-tert-octyl trimelitate, etc.), an ester of benzoic acid (such as 2-ethylhexyl benzoate, etc.), an ester of phosphoric acid (such as diphenyl phosphate, triphenyl phosphate, tricresyl phosphate, dioxtyl butyl phosphate, etc.), an ester of citric acid (such as tributyl acetyl citrate, etc.), an alkylamide (such as N,N-diethyl laurylamide, etc.), and the like, or in an organic solvent having a boiling point of about 30° to about 150° C, for example, a lower alkyl acetate (such as ethyl acetate, butyl acetate, etc.), ethyl propionate, secondary butyl alcohol, methyl isobutyl ketone, β-ethoxyethyl acetate, methyl Cellosolve acetate, and the like, and then the solution is dispersed in a hydrophilic colloid. The high boiling organic solvent and the low boiling organic solvent described above can be used in admixture.

A coupler having an acid group such as a carboxylic acid or a sulfuric acid group can be incorporated in a hydrophilic colloid as an aqueous alkaline solution thereof.

These dye-forming and colored couplers are generally used in a range from $2 \times 10^{-3}$ to $3 \times 10^{-1}$ mol, preferably from $1 \times 10^{-2}$ to $5 \times 10^{-1}$ mol per mol of silver in the emulsion layer.

When a color light-sensitive material is developed in the presence of the DIR coupler of the present invention, the color processing essentially comprises a color development, a bleaching and a fixing step. Each step can be carried out individually. Two or more of these steps can be carried out in a single step by using a processing solution with two or more functions, such as a monobath bleach-fixing solution. Each of the processing steps may be divided into two or more substeps, and it is also possible to employ a combination of processings comprising a color development, a first fixing and a bleach-fixing. In addition to the above described steps, a color processing can comprise steps such as pre-hardening, neutralizing, first development (black and white development), stabilizing and washing, depending on the need. The processing temperature may be varied depending on the kind of light-sensitive material to be processed or the type of processing. Color processing may be carried out at a temperature below about 18° C, but in most cases it is conducted at a temperature above about 18° C, particularly 20° to 60° C. In recent years, color processings have often been carried out at a temperature of from 30° to 60° C. It is not necessary to conduct all processing steps at the same temperature.

A color developer solution is an aqueous alkaline solution containing a developing agent and having a pH greater than about 8, preferably between 9 and 12. The developing agent is a compound which has a primary amino group on an aromatic ring and which is capable of developing exposed silver halide or a precursor which provides such a compound. Preferred examples of developing agents are, for example, 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methansulfonamidoethylaniline, 4-amino-N,N-dimethylaniline, 4-amino-3-methoxy-N,N-diethylaniline, 4-amino-3-methyl-N-ethyl-N-β-methoxyethylanilien, 4-amino-3-methoxy-N-ethyl-N-β-methoxyethylaniline, 4-amino-3-β-methanesulfonamidoethyl-N,N-diethylaniline, and the salts thereof (for example, sulfates, hydrochlrides, sulfites, p-toluenesulfonates, etc.). Other examples are described for example, in U.S. Pat. Nos. 2,193,015 and 2,592,364; Japanese Patent Application (OPI) No. 64933/1973; and L. F. A. Mason, *Photographic Processing Chemistry*, Focal Press, London (1966), pp. 226-229. The above-described compounds may be used together with 3-pyrazolidones, if desired. If desired, various additives may be added to the color developer solution. Examples of such additives include alkaline agents (e.g., hydroxides, carbonates and phosphates of alkali metals or ammonia), pH adjusting agents or buffers (e.g., weak acids or bases, such as acetic acid and boric acid, or the salts thereof), development promoters (e.g., compounds described in U.S. Pat. Nos. 2,648,604; 3,671,247; 2,533,990; 2,577,127 and 2,950,970, British Pat. Nos. 1,020,033 and 1,020,032; U.S. Pat. No. 3,068,097, etc.), antifogging agents (e.g., alkali metal bromides and alkali metal iodides; nitrobenzoimidazoles, such as those described in U.S. Pat. Nos. 2,496,940 and 2,656,271; mercaptobenzimidazole, 5-methylbenzotriazole, 1-phenyl-5-mercaptotetrazole; the antifogging agents described in U.S. Pat. Nos. 3,113,864; 3,342,596; 3,295,976; 3,615,522 and 3,597,199; British Pat. No. 972,211; Japanese Patent Publication No. 41675/1971, and *Kagaku Shashin Binran (A Handbook of Scientific Photography)*, Vol. II, pp. 29-47, stain or sludge preventing agents (e.g., those described in U.S. Pat. Nos. 3,161,513 and 3,161,514; British Pat. Nos. 1,030,442; 1,144,481; and 1,251,558), and preservatives (e.g., sulfites, bisulfites, hydroxylamine hydrochloride, formsulfite, alkanolamine-sulfite adducts, and the like).

In the course of color processing, an intensification processing can be conducted as described in German Patent Application (OLS) No. 2,226,770; U.S. Pat. No. 3,826,652, etc.

In the case of a black-and-white development, any known developing agent or combination thereof may be used. The processing solution used can contain almost the same additives as those used in a color processing solution.

The amount of the DIR coupler of the present invention used varies depending on the type of light-sensitive material and processing, but ordinarily they can be incorporated with advantage into a light-sensitive material at a concentration of about 0.00001 mole to about 0.5 mol per mole of silver halide contained in the emulsion, and can be added to a developer solution at a concentration of about $1 \times 10^{-4}$ to about $1 \times 10^{-1}$ mole per 1000 ml of the developer solution.

Silver halide photographic emulsions used in the present invention are those in which light-sensitive silver halides such as silver chloride, silver bromide, silver chlorobromide, silver chloroiodide, silver iodobromide and silver chloroiodobromide are dispersed in a hydrophilic high molecular weight substance (protective colloid), such as gelatin etc., and can be prepared by various methods. Various conventional additives for ordinary silver halide photographic emulsions such as chemical sensitizers, stabilizers, antifogging agents, hardeners, spectral sensitizers, surface active agents, etc., can be incorporated in the silver halide photographic emulsion. The photographic emulsions can be coated on an appropriate photographic support by a known method.

A suitable coating amount of silver halide can range from about $1 \times 10^{-4}$ to about $1 \times 10^{-2}$ mol/m².

Preferred examples of the photographic supports are a film of synthetic and semi-synthetic polymers such as cellulose acetate, polyethylene, polyethylene terephthalate, polycarbonate, etc. a paper coated or laminated with a baryta layer or an α-olefin polymer (for example, polyethylene, polypropylene, a copolymer of ethylene and butene, etc.) and the like.

The DIR coupler of the present invention can be used for various kinds of silver halide photographic light-sensitive materials. For example, the compound can be employed with silver halide photographic light-sensitive materials used for various purposes such as conventional black and white light-sensitive materials, lithographic black and white light-sensitive materials, light-sensitive materials for X-ray or electron beam recording, black and white light-sensitive materials having high resolving power, conventional color light-sensitive materials, color light-senitive materials for X-ray, light-sensitive materials for the color diffusion transfer process, and the like.

According to one embodiment of the present invention, in a multilayer color light-sensitive material which comprises a support having thereon a blue-sensitive emulsion layer unit comprising at least one silver halide emulsion layer which is mainly sensitive to blue light (wavelength region of about 500 nm or below) and contains a yellow color coupler capable of forming a yellow dye upon coupling with an oxidation product of an aromatic primary amine developing agent, a green-sensitive emulsion layer unit comprising at least one silver halide emulsion layer which is mainly sensitive to green light (wavelength region of about 500 to 600 nm) and contains a magenta color coupler capable of forming a magenta dye upon coupling with an oxidation product of an aromatic primary amine developing agent and a red-sensitive emulsion layer unit comprising at least one silver halide emulsion layer which is sensitive to red light (wavelength region of about 590 nm or more) and contains a cyan color coupler capable of forming a cyan dye upon coupling with an oxidation product of an aromatic primary amine developing agent, and optionally a photographic subsidiary layer such as an intermediate layer, the DIR coupler of the present invention can be incorporated into the emulsion layer or the intermediate layer.

In the above-described embodiment, each emulsion layer of the blue-sensitive emulsion layer unit, the green-sensitive emulsion layer unit and red-sensitive emulsion layer unit can be positioned in various orders depending on the purpose of the use of the light-sensitive material. For example, when each emulsion layer unit is composed of one emulsion layer, a red-sensitive emulsion layer, a green-sensitive emulsion layer and a blue-sensitive emulsion layer are positioned in this order from a support or these layers can be interchanged to another order. Also, when an emulsion layer unit is composed of two or more emulsion layers, these emulsion layers can be positioned either contiguous to each other or separated by an emulsion layer of another emulsion layer unit.

A multilayer color light-sensitive material which comprises a support having thereon a red-sensitive silver halide photographic emulsion layer unit containing a diffusion resistant uncolored cyan coupler and a diffusion resistant colored cyan coupler both of which can provide a cyan image upon color development, a green-sensitive silver halide photographic emulsion layer unit containing a diffusion resistant uncolored magenta coupler and a diffusion resistant colored magenta coupler both of which can provide a magenta image upon color development and a blue-sensitive silver halide photographic emulsion layer unit containing a diffusion resistant uncolored yellow coupler which can provide a yellow image upon color development and the red-sensitive emulsion layer unit, the green-sensitive emulsion layer unit, the blue-sensitive emulsion layer unit or an intermediate layer contains the DIR coupler of the present invention, is also useful.

The DIR coupler of the present invention, even in a small amount (3.g., 0.5 to 5 mol%), can provide excellent development inhibiting effects which result in a control of the image tone, a reduction in graininess of the image, an improved sharpness of the image and improved color reproducibility. In particular, the DIR coupler of the present invention provides exceptionally large effects on improving sharpness of the image due to edge effects within a layer containing the DIR coupler or within a layer directly adjacent thereto. The DIR coupler of the present invention is far superior with respect to this point to known DIR couplers as described in U.S. Pat. Nos. 3,148,062; 3,227,554; 3,617,291 and 3,701,783; U.S. Pat. No. 3,933,500 coresponding to Japanese Patent Application (OPI) No. 122335/1974 and German Patent Application (OLS) No. 2,329,587 corresponding to Japanese Patent Publication No. 34232/1975, which will be apparent from the examples described hereinafter. The DIR coupler of the present invention is also more effective in reducing the graininess of the image than these known DIR couplers. Further, the DIR coupler of the present invention is superior to DIR couplers described in Japanese Patent Application (OPI) No. 122335/1974 with respect to interlayer color correction effects. Moreover, the DIR coupler of the present invention is stable when incorporated in a light-sensitive emulsion layer and does not adversely affect the durability of the light-sensitive material. It can be used without concern. Furthermore, the photographic developing agent of the present invention can be prepared very easily as described in the Synthesis Examples hereinbefore.

The present invention will further illustrated by reference to the following examples, but the present invention should not be construed as being limited to the following examples.

EXAMPLE I

Sample 101: On a transparent cellulose triacetate film support were coated the following first layer to fourth layer in this order and dried to prepare the sample. The composition and method for preparation of the coating solutions used for each layer were as follows.

First Layer: Red-Sensitive Emulsion Layer

One kg of a high speed silver iodobromide emulsion (silver content: 0.6 mol, iodide content: 6 mol%) was spectrally sensitized using $4 \times 10^{-5}$ mol of Sensitizing Dye I and $1 \times 10^{-5}$ mol of Sensitizing Dye II per mol of silver, respectively. 550 g of Dispersion I prepared by dissolving 100 g of Coupler A into 100 cc of tricresyl phosphate and 200 cc of ethyl acetate, and then dispersing the resulting solution into 1 kg of a 10% aqueous gelatin solution using 4 g of sodium nonylbenzenesulfonate (surface active agent) was added to the spectrally sensitized silver iodobromide emulsion and stirred. To the mixture there was added as a hardener an aqueous solution of 2 g of sodium 2,4-dichloro-6-hydroxytriazine. The thus prepared coating solution was coated on a transparent cellulose triacetate film support at a silver coated amount of 1.5 g/m².

Second Layer: Intermediate Layer 50 g of 2,5-di-tert-octylhydroquinone was dissolved in 100 cc of tricresyl phosphate and dipsered in 1 kg of a 10% aqueous gelatin solution in the same manner as described for Dispersion I. 250 g of the thus prepared dispersion and an aqueous solution of 2 g of sodium 2,4-dichloro-6-hydroxytriazine were added to 1 kg of a 10% aqueous gelatin solution and stirred. The coating solution was coated at a dry thickness of 1.5 microns.

Third Layer: Green-Sensitive Emulsion Layer 1 kg of a high speed silver iodobromide emulsion (same as used in the First Layer) was spectrally sensitized using 3 × 10⁻⁵ mol of Sensitizing Dye III and 1 × 10⁻⁵ mol of Sensitizing Dye IV per mole of silver, respectively. Using 100 g of Coupler B, Dispersion II was prepared in the same manner as described for Dispersion I. 700 g of Dispersion II was added to the spectrally sensitized silver iodobromide emulsion and an aqueous solution of 2 g of sodium 2,4-dichloro-6-hydroxytriazine was added thereto with stirring.

Sensitizing Dye IV: Sodium salt of anhydro-5,6,5,6-tetrachloro-1,1-diethyl-3,3-sulfopropoxyethoxyethylimidazolocarbocyanine hydroxide Coupler A: 1-Hydroxy-N-[γ-(2,4-di-tert-amylphenoxy)-propyl]-2-naphthamide Coupler B: 1-(2,4,6-Trichlorophenyl)-3-[3-(2,4-di-tert-amylphenoxyacetamido)benzamido]-5-pyrazolone (a 4-equivalent coupler)

Comparison DIR Coupler D-1

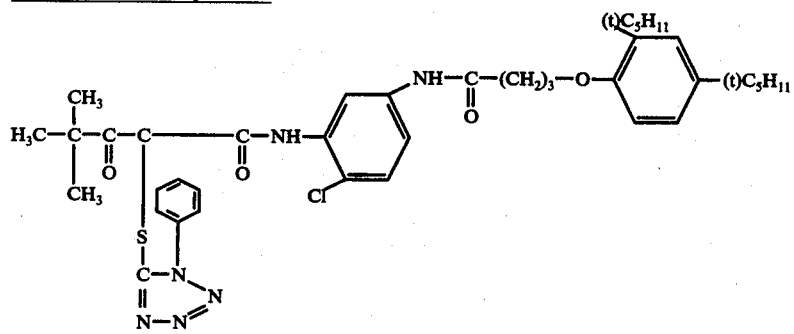

Comparison DIR Coupler D-2

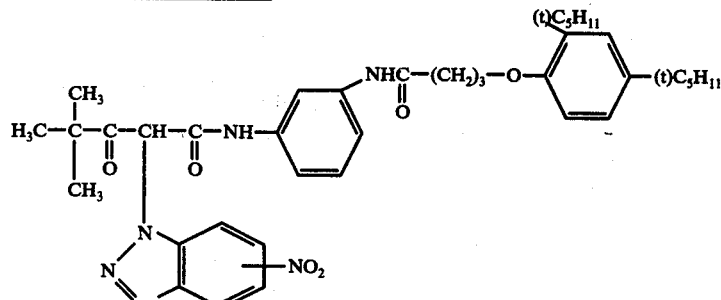

Comparison DIR Coupler D-3

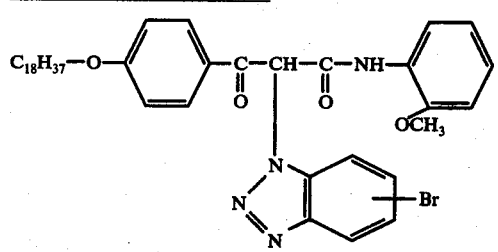

Fourth Layer: Protective Layer

To 1 kg of a 10% aqueous gelatin solution was added 2 g of sodium 2,4-dichloro-6-hydroxytriazine. The solution was coated at a dry thickness of 1.5 microns.

Samples 102 to 109: Samples 102 to 109 were prepared in the same manner as Sample 101 except that a DIR coupler was additionally added in an amount of corresponding to 3 mol% of the amount of Coupler B to the oil (coupler solvent) in Dispersion II of Sample 101 and the coating amount of the Third Layer was adjusted so as to provide the same γG as Sample 101.

The compounds used in the preparation of the abovedescribed samples were:

Sensitizing Dye I: Pyridinium salt of anhydro-5,5'-dichloro-3,3'-di-sulfopropyl-9-ethyl-thiacarbocyanine hydroxide.

Sensitizing Dye II: Triethylamine salt of anhydro-O-ethyl-3,3'-di-(3-sulfopropyl)-4,5,4',5'-dibenzothiacarbocyanine hydroxide Sensitizing Dye III: Sodium salt of anhydro-9-ethyl-5,5'-dichloro-3,3'-sulfopropyloxacarbocyanine Samples 101 to 109 were exposed stepwise using green light and then exposed uniformly using red light, and subjected to the following processing steps at 38° C. In addition, these samples were line image exposed to soft X-rays through a slit with a 4 mm width and a slit with a 10 μm width and subjected to the same processing as above.

| | |
|---|---|
| 1. Color Development | 3 min. and 15 sec. |
| 2. Bleaching | 6 min. and 30 sec. |
| 3. Washing | 3 min. and 15 sec. |
| 4. Fixing | 6 min. and 30 sec. |
| 5. Washing | 3 min. and 15 sec. |
| 6. Stabilizing | 3 min. and 15 sec. |

The processing solutions used in the above steps had the following compositions:

| Color Developer Solution | | |
|---|---|---|
| Sodium Nitrilotriacetate | 1.0 | g |
| Sodium Sulfite | 4.0 | g |
| Sodium Carbonate | 30.0 | g |

| | -continued | |
|---|---|---|
| Potassium Bromide | 1.4 | g |
| Hydroxylamine Sulfate | 2.4 | g |

Table 1

| Sample No. | | DIR Material | | γG | Interimage Effects (γR/γG) | Edge Effects $(D_1^G-D_2^G)D_1^G$ | RMS Graininess** $D_G = 0.5$ |
|---|---|---|---|---|---|---|---|
| | | Compound | Amount* (mol%) | | | | |
| 101 | (Control) | — | — | 1.30 | 0.06 | 0.04 | 0.061 |
| 102 | (This invention) | Comp. (11) | 3 | 1.34 | −0.48 | 0.33 | 0.045 |
| 103 | " | Comp. ( 7) | 3 | 1.29 | −0.45 | 0.34 | 0.038 |
| 104 | " | Comp. (18) | 3 | 1.27 | −0.34 | 0.32 | 0.044 |
| 105 | " | Comp. ( 2) | 3 | 1.28 | −0.47 | 0.35 | 0.039 |
| 106 | " | Comp. ( 9) | 3 | 1.28 | −0.36 | 0.30 | 0.046 |
| 107 | (Comparison) | DIR Coupler D-1 | 10 | 1.26 | −0.13 | 0.13 | 0.050 |
| 108 | " | DIR Coupler D-2 | 3 | 1.25 | −0.15 | 0.17 | 0.057 |
| 109 | " | DIR Coupler D-3 | 3 | 1.32 | −0.15 | 0.13 | 0.060 |

*Amount: mol% to Coupler B
**RMS Graininess: measured with a slit of 10μm × 10 μm.

| 4-(N-Ethyl-N-β-hydroxyethylamino)-2-methylaniline Sulfate | 4.5 | g |
|---|---|---|
| Water to make | 1 | liter |
| Bleaching Solution | | |
| Ammonium Bromide | 160.0 | g |
| Ammonia (28% aq. soln) | 25.0 | ml |
| Sodium Ethylenediaminetetra Acetate-Iron (II) Salt Complex | 130 | g |
| Acetic Acid (glacial) | 14 | ml |
| Water to make | 1 | liter |
| Fixing Solution | | |
| Sodium Tetrapolyphosphate | 2.0 | g |
| Sodium Sulfite | 4.0 | g |
| Ammonium Thiosulfate (70% aq. soln.) | 175.0 | ml |
| Sodium Bisulfite | 4.6 | g |
| Water to make | 1 | liter |
| Stabilizing Solution | | |
| Formaldehyde (38% aq. soln.) | 8.0 | ml |
| Water to make | 1 | liter |

In the characteristic curve thus obtained, when the gradation of the curve of the red filter optical density vs. log (exposure amount) (which corresponds to the First Layer) is designated γR and the gradation of the curve of the green filter optical density vs. log (exposure amount) (which corresponds to the Third Layer) is designated γG, the value of γR/γG is considered the amount of interimage effects from the Third Layer to the First Layer (γR values of the samples are substantially constant). That is, the value of γR/γG is minus and the greater the absolute value the larger are the interimage effects. The γR/γG value of each sample is shown in Table 1.

The optical density of each sample obtained by line image exposure with soft X-rays was measured by microdensitometer traces with green light. When the density of the line image with a 10 μm width is designated $D_1^G$ and the density of the line image with a 4 mm width is designated $D_2^G$, the value of $(D_1^G - D_2^G)/D_1^G$ means the amount of edge effects of the sample when the sample is observed with red light. The value of $(D_1^G - D_2^G)/D_1^G$ of each sample is shown in Table 1.

Furthermore, each sample was exposed stepwise with white-light, processed in the same manner as described in Example 1 and the graininess of the color image thereof was measured using the conventional RMS (Root Mean Square) method using green light. The results of RMS graininess at a density of 0.5 are shown in Table 1.

The measurement of the graininess of the RMS method is well known in the photographic art and is described in *Photographic Science and Engineering*, vol. 19, No. 4, pp. 235 to 238 (1975), D. Zeick & B. L. Brothers, Jr. RMS Granulality; "Determination of Just-noticeakle Difference".

A smaller numerical value in the table above shows better graniness.

From the results described above, it is apparent that Compounds (2), (7), (9), (11) and (18) of the present invention provide larger interimage effects and edge effects and more improved graininess in comparison with Comparison DIR Couplers D-2 and D-3, and provide superior properties in a smaller amount than that of Comparison DIR Coupler D-1 and thus have exceptionally good properties as DIR couplers.

EXAMPLE 2

Sample 201: The sample was prepared in the same manner as Sample 101 in Example 1.

Sample 202: The sample was prepared in the same manner as Sample 201 except that Compound (23) of the present invention was further added in an amount of 3 mol% per mol of Coupler B to the oil (coupler solvent) in Dispersion II added to the Third Layer of Sample 201.

Sample 203: The sample was prepared in the same manner as Sample 202 except that Comparison DIR Coupler D-4 was used in an amount of 3 mol% per mol of Coupler B in place of Compound (23).

Comparison DIR Coupler D-4:

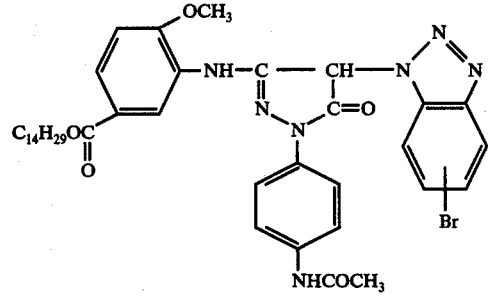

Samples 201, 202 and 203 were exposed and processed in the same manner as described in Example 1 and the γG, γR/γG, RMS, $(D_1^G - D_2^G)/D_1^G$ of these samples were determined. The results are shown in Table 2 below.

| Sample No. | DIR Material Compound | $\gamma G$ | Inter-Image $\gamma R/\gamma G$ | Edge $(D_1{}^G\text{-}D_2{}^G)/D_1{}^G$ | RMS $D_G=0.5$ |
|---|---|---|---|---|---|
| 201 | — | 1.32 | 0.03 | −0.01 | 0.063 |
| 202 | Compound (23) | 1.35 | −0.49 | 0.34 | 0.036 |
| 203 | DIR Coupler D-4 | 1.32 | −0.10 | 0.14 | 0.055 |

From the results described above it is apparent that Compound (23) of the present invention provides superior properties with respect to interimage effects, edge effects and graininess and is more useful as a DIR coupler in comparison with DIR Coupler D-4.

While the invention has been described in detail and with reference to specific embodiments thereof, it will be apparent to one skilled in the art that various changes and modifications can be made therein without departing from the spirit and scope thereof.

What is claimed is:

1. A silver halide photographic element comprising a silver halide emulsion layer containing a photographic coupler capable of releasing a development inhibitor upon reaction with an oxidation product of a color developing agent and represented by the following general formula (I)

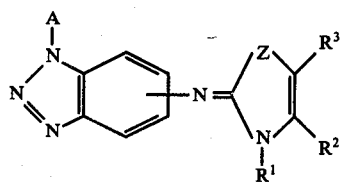

(I)

wherein A represents a coupler residue substituted in the coupling off position with the benzotriazole moiety shown in the formula; Z represents a sulfur atom, a selenium atom or an oxygen atom; $R^1$ represents an aliphatic group; and $R^2$ and $R^3$, which may be the same or different, each represents a hydrogen atom, an aliphatic group, an alkoxy group, a hydroxy group, or an aromatic group or $R^2$ and $R^3$ can combine and represent the atoms necessary to form a benzene ring or a naphthalene ring; or represented by the following heneral formula (II)

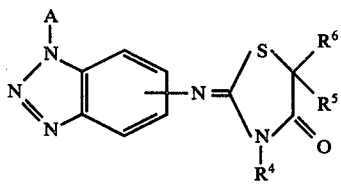

(II)

wherein A represents a coupler residue substituted in the coupling off position with the benzotriazole moiety shown in the formula; $R^4$ represents an aliphatic group or an aromatic group; and $R^5$ and $R^6$, which may be the same or different, each represents a hydrogen atom, an aliphatic group or an aromatic group.

2. The silver halide photographic element as claimed in claim 1, wherein said aliphatic group represented by $R^2$ is an unsubstituted alkyl group having 1 to 18 carbon atoms or a substituted alkyl group having 1 to 12 carbon atoms in the alkyl moiety thereof.

3. The silver halide photographic element as claimed in claim 1, wherein said aliphatic group represented by $R^3$ is an unsubstituted alkyl group having 1 to 18 carbon atoms or a substituted alkyl group having 1 to 12 carbon atoms in the alkyl moiety thereof.

4. The silver halide photographic element as claimed in claim 1, wherein said aromatic group represented by $R^2$ is a monocyclic or bicyclic aryl group.

5. The silver halide photographic element as claimed in claim 1, wherein said aromatic group represented by $R^3$ is a monocyclic or bicyclic aryl group.

6. The silver halide photographic element as claimed in claim 1, wherein said alkoxy group represented by $R^2$ has 1 to 18 carbon atoms.

7. The silver halide photographic element as claimed in claim 1, wherein said alkoxy group represented by $R^3$ has 1 to 18 carbon atoms.

8. The silver halide photographic element as claimed in claim 1, wherein $R^2$ and $R^3$ form a benzene ring.

9. The silver halide photographic element as claimed in claim 8, wherein Z represents a sulfur atom.

10. The silver halide photographic element as claimed in claim 1, wherein said coupler is represented by the following formula

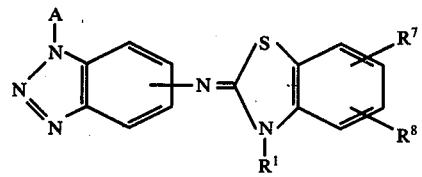

(Ia)

wherein A and $R^1$ each has the same meaning as in claim 1; $R^7$ and $R^8$, which may be the same or different, each represents a hydrogen atom, a halogen atom, an aliphatic group, an alkoxy group, a hydroxy group, a nitro group, a carboxyl group, an alkoxycarbonyl group, an acylamino group or a sulfonamido group.

11. The silver halide photographic element as claimed in claim 10, wherein said aliphatic group represented by $R^1$ is an alkyl group having 1 to 18 carbon atoms or an aralkyl group having 7 to 16 carbon atoms.

12. The silver halide photographic element as claimed in claim 10, wherein $R^7$ and $R^8$, each represents a hydrogen atom, a chlorine atom, a methyl group, an ethyl group, a methoxy group, an ethoxy group or a hydroxy group.

13. The silver halide photographic element as claimed in claim 10, wherein A is represented by the following general formula (III)

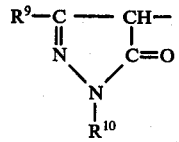

(III)

wherein $R^9$ represents a hydroxy group, an alkyl group, an aryl group, an amino group, a carbonamido group, a sulfonamido group, a ureido group or an alkoxy group; $R^{10}$ represents a hydrogen atom, an alkyl group, an aryl group, or a 5- or 6-membered heterocyclic group containing one or more of a nitrogen or an oxygen atom; or is represented by the general formula (IV)

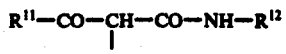 (IV)

wherein $R^{11}$ represents an alkyl group, an aryl group or an amino group; and $R^{12}$ represents an aryl group.

14. The silver halide photographic element as claimed in claim 13, wherein $R^9$ represents a hydroxy group, has up to 22 carbon atoms and represents an alkoxy group, an alkyl group, an alkylamino group or an alkylcarbonamido group, or has 6 to 32 carbon atoms and represents an aryl group, an arylamino group or an arylcarbonamido group; and $R^{10}$ represents an aryl group having 6 to 32 carbon atoms.

15. The silver halide photographic element as claimed in claim 13, wherein $R^{11}$ represents a tertiary alkyl group having 4 to 18 carbon atoms or a monocyclic aryl group having 6 to 40 carbon atoms; and $R^{12}$ represents a monocyclic aryl group having 6 to 40 carbon atoms.

* * * * *